(12) United States Patent
Williams et al.

(10) Patent No.: US 9,322,817 B2
(45) Date of Patent: Apr. 26, 2016

(54) SOIL TESTING SYSTEMS AND METHODS THEREOF

(71) Applicant: Luster Leaf Products, Inc., Woodstock, IL (US)

(72) Inventors: Mark B. Williams, Half Moon Bay, CA (US); Larry L. Holbein, Woodstock, IL (US); Christopher G. Holbein, Woodstock, IL (US)

(73) Assignee: Luster Leaf Products, Inc., Woodstock, IL (US)

( * ) Notice: Subject to any disclaimer, the term of this patent is extended or adjusted under 35 U.S.C. 154(b) by 7 days.

(21) Appl. No.: 14/270,938

(22) Filed: May 6, 2014

(65) Prior Publication Data

US 2014/0329330 A1    Nov. 6, 2014

Related U.S. Application Data

(60) Provisional application No. 61/819,873, filed on May 6, 2013.

(51) Int. Cl.
| | |
|---|---|
| *G01N 33/24* | (2006.01) |
| *G01N 21/59* | (2006.01) |
| *G01N 21/17* | (2006.01) |
| *G01N 21/77* | (2006.01) |
| *G01N 21/25* | (2006.01) |

(52) U.S. Cl.
CPC ............. *G01N 33/24* (2013.01); *G01N 21/59* (2013.01); *G01N 21/77* (2013.01); *G01N 21/255* (2013.01); *G01N 2033/245* (2013.01); *G01N 2201/0221* (2013.01); *G01N 2201/0627* (2013.01); *Y10T 436/15* (2015.01); *Y10T 436/173076* (2015.01); *Y10T 436/20* (2015.01)

(58) Field of Classification Search
CPC ....... G01N 33/24; G01N 33/00; G01N 21/59; G01N 21/17; G01N 21/00; G01N 21/77; G01N 21/75; G01N 21/255; G01N 21/25; Y10T 436/15; Y10T 436/20; Y10T 436/17; Y10T 436/173076; Y10T 436/00
USPC ............. 436/127, 110, 106, 100, 82.9, 82.05, 436/68.1, 50; 422/82.9, 82.05, 68.1, 50, 422/127, 110, 106, 100
See application file for complete search history.

(56) References Cited

U.S. PATENT DOCUMENTS 4,126,417 A * 11/1978 Edwards ...................... 422/401
6,403,037 B1 * 6/2002 Chang et al. ................. 422/68.1

* cited by examiner

*Primary Examiner* — Christine T Mui
(74) *Attorney, Agent, or Firm* — Amster, Rothstein & Ebenstein, LLP

(57) ABSTRACT

A soil tester is disclosed, and comprises a housing and a sampling apparatus. The housing includes an interior sampling chamber configured to receive a sample container. The sampling apparatus comprises a photodetector and a light source. The photodetector is mounted along a portion of the interior sampling chamber and has a variable resistance determined by a property of incident light. The light source is mounted to the interior sampling chamber in a transmissive orientation relative to the photodetector so that a beam of light can be transmitted from the light source to the photodetector through the interior sampling chamber. A display on the housing is responsive to the photodetector.

18 Claims, 13 Drawing Sheets

| NAME | pH | NAME | pH | NAME | pH |
|---|---|---|---|---|---|
| FRUIT | | VEGETABLES & HERBS | | | |
| APPLE | 5.0 - 6.5 | ARTICHOKE | 6.5 - 7.5 | PEPPERMINT | 6.0 - 7.5 | 
| APRICOT | 6.0 - 7.0 | ASPARAGUS | 6.0 - 8.0 | PISTACHIO | 5.0 - 6.0 |
| AVOCADO | 6.0 - 7.5 | BASIL | 5.5 - 6.5 | POTATO | 4.5 - 6.0 |
| BANANA | 5.0 - 7.0 | BEAN | 6.0 - 7.5 | POTATO - SWEET | 5.5 - 6.0 |
| BLACKBERRY | 5.0 - 6.0 | (Runner, Broad, French) | | PUMPKIN | 6.0 - 7.0 |
| BLUEBERRY | 4.0 - 6.0 | BEETROOT | 6.0 - 7.5 | RADISH | 5.5 - 7.5 |
| CANTALOUPE | 6.5 - 7.5 | BROCCOLI | 6.0 - 7.0 | RICE | 6.0 - 7.0 |
| CHERRY | 6.0 - 7.5 | BRUSSELS SPROUTS | 6.0 - 7.5 | ROSEMARY | 5.0 - 6.5 |
| CRANBERRY | 5.5 - 6.5 | CABBAGE | 6.0 - 7.5 | SAGE | 5.5 - 6.5 |
| CURRENT: Black | 6.0 - 8.0 | CALABRESE | 6.5 - 7.5 | SHALLOT | 5.5 - 7.0 |
| Red | 6.0 - 7.0 | CARROT | 5.5 - 7.0 | SORGHUM | 5.5 - 7.5 |
| White | 6.0 - 8.0 | CAULIFLOWER | 5.5 - 7.5 | SOYBEAN | 5.5 - 6.5 |
| | | CELERY | 6.0 - 7.0 | SPEARMINT | 5.0 - 6.5 |
| DAMSON | 6.0 - 7.5 | CHICORY | 5.0 - 6.5 | SPINACH | 5.5 - 7.5 |
| GOOSEBERRY | 5.0 - 6.5 | CHINESE CABBAGE | 6.0 - 7.5 | SWEDE | 6.0 - 7.5 |
| GRAPEVINE | 6.0 - 7.0 | CHIVES | 6.0 - 7.0 | THYME | 5.5 - 7.0 |
| GRAPEFRUIT | 6.0 - 7.5 | CORN - SWEET | 5.5 - 7.5 | TOMATO | 5.5 - 7.5 |
| HAZELNUT | 6.0 - 7.5 | CRESS | 6.0 - 7.0 | TURNIP | 5.5 - 7.0 |
| HOP | 6.0 - 7.5 | COURGETTES | 5.5 - 7.5 | WATER CRESS | 6.0 - 8.0 |
| HUCKLEBERRY | 4.0 - 6.0 | CUCUMBER | 5.0 - 6.0 | | |
| LEMON | 6.0 - 7.0 | FENNEL | 5.5 - 7.5 | HOUSE & GREENHOUSE PLANT | |
| LYCHEE | 5.5 - 6.5 | GARLIC | 5.0 - 7.0 | ABUTILON | 5.5 - 6.5 |
| MANGO | 5.0 - 6.0 | GINGER | 6.0 - 8.0 | ACORUS | 5.0 - 6.5 |
| MELON | 5.5 - 6.5 | HORSERADISH | 6.0 - 7.0 | AECHMEA | 5.0 - 6.5 |
| MULBERRY | 6.0 - 7.5 | KALE | 6.0 - 7.5 | AFRICAN VIOLET | 6.0 - 7.0 |
| NECTARINE | 6.0 - 7.5 | KOHLRABI | 6.0 - 7.5 | AGLAONEMA | 5.0 - 6.0 |
| PEACH | 6.0 - 7.5 | LEEK | 6.0 - 8.0 | AMARYLIS | 5.5 - 6.5 |
| PEAR | 6.0 - 7.5 | LENTIL | 5.5 - 7.0 | ANTHURIUM | 5.0 - 6.0 |
| PINEAPPLE | 5.0 - 6.0 | LETTUCE | 6.0 - 7.0 | APHELANDRA | 5.0 - 6.0 |
| PLUM | 6.0 - 7.5 | MARJORAM | 6.0 - 8.0 | ARAUCARIA | 5.0 - 6.0 |
| POMEGRANATE | 5.5 - 6.5 | MARROW | 6.0 - 7.5 | ASPARAGUS FERN | 6.0 - 8.0 |
| QUINCE | 6.0 - 7.5 | MILLET | 6.0 - 6.5 | ASPIDISTRA | 4.0 - 5.5 |
| RASPBERRY | 5.0 - 7.5 | MINT | 7.0 - 8.0 | AZALEA | 4.5 - 6.0 |
| RHUBARB | 5.5 - 7.0 | MUSHROOM | 6.5 - 7.5 | BABY'S BREATH | 6.0 - 7.5 |
| STRAWBERRY | 5.0 - 7.5 | MUSTARD | 6.0 - 7.5 | BABY'S TEARS | 5.0 - 6.0 |
| WATERMELON | 5.5 - 6.5 | OLIVE | 5.5 - 6.5 | BEGONIA | 5.5 - 7.0 |
| | | ONION | 6.0 - 7.0 | BIRD OF PARADISE | 6.0 - 6.5 |
| | | PAPRIKA | 7.0 - 8.5 | BISHOP'S CAP | 6.0 - 7.5 |
| | | PARSLEY | 5.0 - 7.0 | BLACK-EYED SUSAN | 5.0 - 6.0 |
| | | PARSNIP | 5.5 - 7.0 | BLOOD LEAF | 5.5 - 7.0 |
| | | PEA | 6.0 - 7.5 | BOTTLEBRUSH | 6.5 - 6.5 |
| | | PEANUT | 5.0 - 6.5 | BOUGAINVILLEA | 6.0 - 7.5 |
| | | PECAN | 4.0 - 6.0 | BOXWOOD | 5.5 - 7.5 |
| | | PEPPER | 5.5 - 7.0 | | |

| NAME | pH |
|---|---|
| BROMELIADS | 5.0 - 7.5 |
| BUTTERFLY FLOWER | 6.0 - 7.5 |
| CACTI | 4.5 - 6.0 |
| CALCAOLARIA | 6.0 - 7.0 |
| CALADIUM | 6.0 - 6.0 |
| CALLA LILY | 6.0 - 7.0 |
| CAMELIA | 4.5 - 5.5 |
| CAMPANULA | 5.5 - 6.5 |
| CAPSICUM | 5.0 - 6.5 |
| CARDINAL FLOWER | 6.0 - 6.0 |
| CASTOR OIL PLANT | 5.5 - 6.5 |
| CANTURY PLANT | 5.0 - 6.5 |
| CHINESE EVERGREEN | 5.0 - 6.0 |
| CHINESE PRIMROSE | 6.0 - 7.5 |
| CHRISTMAS CACTUS | 5.0 - 6.5 |
| CINERARIA | 5.5 - 7.0 |
| CLERODENDRUM | 5.0 - 6.0 |
| OLIVIA | 5.5 - 6.5 |
| COCKSCOMB | 6.0 - 7.0 |
| COFFEE PLANT | 5.0 - 6.0 |
| COLEUS | 6.0 - 7.0 |
| COLUMNEA | 4.5 - 5.5 |
| CORAL BERRY | 5.5 - 7.5 |
| CRASSULA | 5.5 - 6.0 |
| CREEPING FIG | 5.0 - 6.0 |
| CROTON | 5.0 - 6.0 |
| CROWN OF THORNS | 6.0 - 7.5 |
| CUPHEA | 6.0 - 7.5 |
| CYCLAMEN | 6.0 - 7.0 |
| CYPERUS | 5.0 - 7.5 |
| DIEFFENBACHIA | 5.0 - 6.0 |
| DIPLADENIA | 5.0 - 6.0 |
| DIZGOTHECA | 6.0 - 7.5 |
| DRACAENA | 5.0 - 6.0 |
| EASTER LILY | 6.0 - 7.0 |
| ELEPHANT'S EAR | 5.0 - 6.0 |
| EPISCIA | 5.0 - 7.0 |
| EUONYMOUS | 6.0 - 8.0 |

FIG. 7A

| HOUSE & GREENHOUSE PLANTS | pH | NAME | pH | NAME | pH |
|---|---|---|---|---|---|
| FERNS: | | LANTANA | 5.5-7.0 | FLOWERS, TREES & SHRUBS | |
| BIRD'S NEST | 5.0-6.5 | LAURUS (BAY TREE) | 5.0-6.0 | ABELIA | 6.0-8.0 |
| BOSTON | 5.5-6.5 | LEMON PLANT | 6.0-7.0 | ACACIA | 6.0-8.0 |
| BUTTON | 6.0-8.0 | MIMOSA | 5.0-5.5 | ACANTHUS | 6.0-7.0 |
| CHRISTMAS | 6.0-7.5 | MIND YOUR OWN BUSINESS | 5.0-6.0 | ACONITUM | 5.0-6.0 |
| CLOAK | 6.0-7.5 | MONSTERA | 6.0-8.0 | ADONIS | 6.0-8.0 |
| FEATHER | 5.5-6.5 | MYRTLE | 5.0-8.0 | AGERATUM | 6.0-7.5 |
| HART'S TONGUE | 7.0-8.0 | NEVER NEVER PLANT | 8.0-8.0 | AILANTHUS | 6.0-7.5 |
| HOLLY | 4.5-6.0 | NICODEMA (INDOOR OAK) | 8.0-8.0 | AJUGA | 4.0-6.0 |
| MAIDENHAIR | 6.0-8.0 | NORFOLK ISLAND PINE | 5.0-6.0 | ALTHEA | 6.0-7.5 |
| RABBIT'S FOOT | 6.0-7.5 | OLEANDER | 6.0-7.5 | ALYSSUM | 6.0-7.5 |
| SPLEENWORT | 6.0-7.5 | OPLISMENUS | 5.0-6.0 | AMARANTHUS | 6.0-6.5 |
| | | ORCHID | 4.5-5.5 | ANCHUSA | 6.0-7.5 |
| FIG | 5.0-6.0 | OXALIS | 6.0-8.0 | ANDROSACE | 5.0-6.0 |
| FITTONIA | 5.5-6.5 | PALMS | 6.0-7.5 | ANEMONE | 6.0-7.5 |
| FREESIA | 6.0-7.5 | PANDANUS | 5.0-6.0 | AMYLLIS | 5.0-8.0 |
| GARDENIA | 5.0-6.0 | PEACOCK PLANT | 5.0-8.0 | ARBUTUS | 4.0-6.0 |
| | | PELLIONIA | 5.0-6.0 | ARENARIA | 6.0-8.0 |
| GENISTA | 6.5-7.5 | PEPEROMIA | 5.0-6.0 | ARISTEA | 6.0-7.5 |
| GERANIUM | 6.0-8.0 | PHILODENDRON | 5.0-6.0 | ARMERIA | 6.0-7.5 |
| GLOXINIA | 5.5-6.5 | PILEA | 6.0-8.0 | ARNICA | 5.0-6.5 |
| GRAPE IVY | 5.0-6.5 | PLUMBAGO | 5.5-6.5 | ASPERULA | 6.0-8.0 |
| GRAPE HYACINTH | 6.0-7.5 | PODACARPUS | 6.0-6.5 | ASPHODOLINE | 6.0-8.0 |
| GREVILLEA | 5.5-6.5 | POINTSETTIA | 6.0-7.5 | ASTER | 5.5-7.5 |
| GYNURA | 5.5-6.5 | POLYSCIAS | 6.0-7.5 | AUBRITA | 6.0-7.5 |
| HEDERA (IVY) | 6.0-8.0 | POTHOS | 5.0-6.0 | AZALEA | 4.5-6.0 |
| HELIOTROPIUM | 5.0-6.0 | PRAYER PLANT | 5.0-6.0 | BALLOON FLOWER | 6.0-6.5 |
| HENS AND CHICKENS | 6.0-7.0 | PUNICA | 5.5-6.5 | BAYBERRY | 4.0-6.0 |
| HERRINGBONE PLANT | 6.0-6.0 | SAXIFRAGA | 4.5-7.0 | BERGENIA | 6.0-7.5 |
| HIBISCUS PLANT | 6.0-8.0 | SCINDAPSUS | 6.0-8.0 | BLEEDING HEART | 8.0-7.5 |
| HOYA | 5.0-6.0 | SHRIMP PLANT | 5.0-6.0 | BLUEBELL | 5.0-6.0 |
| IMPATIENS | 5.5-6.5 | SPANISH BAYONET | 6.0-7.5 | BROOM | 6.0-7.0 |
| IVY TREE | 6.0-7.0 | SPIDER PLANT | 6.0-7.5 | BUDDLEIA | 6.0-7.5 |
| JACARANDA | 6.0-7.5 | SUCCULENTS | 5.0-6.5 | BUPHTHALUM | 5.0-6.0 |
| JAPANESE SEDGE | 6.0-8.0 | SYNOGONIUM | 5.0-6.0 | BUTTERFLY BUSH | 4.0-6.0 |
| JASMINUM | 5.5-7.0 | TOLMIEA | 5.0-6.0 | CALENDULA | 5.5-7.0 |
| JERUSALEM CHERRY | 5.5-6.5 | TRADESCANTIA | 5.0-6.0 | CAMASSIA | 6.0-8.0 |
| JESSAMONE | 5.0-6.0 | UMBRELLA TREE | 5.0-7.5 | CANDYTUFT | 5.0-7.5 |
| KALANCHOE | 6.0-7.5 | VENUS FLYTRAP | 4.0-5.0 | CANNA | 6.0-8.0 |
| KANGAROO THORN | 6.0-8.0 | WEEPING FIG | 5.0-6.0 | CANTERBURY BELLS | 7.0-7.5 |
| KANGAROO VINE | 5.0-6.5 | YUCCA | 6.0-7.5 | CARDINAL FLOWER | 4.0-8.0 |
| | | ZEBRINA | 5.0-6.0 | CARNATION | 6.0-7.5 |
| | | | | CATALPA | 6.0-8.0 |

FIG. 7B

| NAME | pH | NAME | pH | NAME | pH |
|---|---|---|---|---|---|
| FLOWERS, TREES & SHRUBS | | | | | |
| CELOSIA | 6.0-7.0 | GLOBULARIA | 5.5-7.0 | PAEONIA | 6.0-7.5 |
| CENTAUREA | 5.0-6.5 | GODETIA | 6.0-7.5 | PANSY | 5.5-7.0 |
| CERASTIUM | 6.0-7.0 | GOLDEN ROD | 5.0-7.0 | PASSION FLOWER | 6.0-8.0 |
| CHRYSANTHEMUM | 6.0-7.0 | GYPSOPHILIA | 6.0-7.5 | PASQUE FLOWER | 6.0-7.0 |
| CISSUS | 6.0-7.5 | HAWTHORN | 6.0-7.0 | PAULOWNIA | 6.0-8.0 |
| CISTUS | 6.0-7.5 | HEATHER | 4.0-6.0 | PENSTEMON | 5.5 0 7.0 |
| CLARKIA | 6.0-6.5 | HELIANTHUS | 5.0-7.0 | PERIWINKLE | 6.0-7.5 |
| CLIANTHUS | 6.0-7.5 | HELLEBORUS | 6.0-7.5 | PETUNIA | 6.0-7.5 |
| CLEMATIS | 5.5-7.0 | HOLLY | 5.0-6.5 | PINKS | 6.0-7.5 |
| COLCHICUM | 5.5-6.5 | HOLLYHOCK | 6.0-8.0 | POLYGONUM | 6.0-7.5 |
| COLUMBINE | 6.0-7.0 | HONEYSUCKLE | 6.0-7.5 | POLYANTHUS | 6.0-7.5 |
| CONVOLVULUS | 6.0-8.0 | HYACINTH | 6.5-7.5 | POPPY | 4.5-8.4 |
| COREOPSIS | 5.0-6.0 | HYDRANGEA (Blue) | 4.0-5.0 | PORTULACA | 5.0-7.0 |
| CORDNILLA | 6.5-7.5 | HYDRANGEA (Pink) | 6.0-7.0 | PRIMROSE | 6.0-7.5 |
| CORYDALIS | 6.0-8.0 | HYDRANGEA (White) | 6.5-8.0 | PRIMULA | 6.0-7.5 |
| COSMOS | 5.0-8.0 | HYPERICUM | 5.5-7.0 | PRIVET | 6.0-8.0 |
| COTTONEASTER | 6.0-8.0 | IRIS | 5.0-6.5 | PRUNELLA | 6.0-6.5 |
| CRAB APPLE | 6.0-7.5 | IVY | 6.0-7.5 | PRUNUS | 6.0-7.0 |
| CROCUS | 6.0-8.0 | JUNIPER | 5.0-6.5 | PYRETHRUM | 6.5-7.5 |
| CYNOGLOSSUM | 6.0-7.5 | KALMIA | 4.5-5.0 | RED HOT POKER | 6.0-7.0 |
| DAFFODIL | 6.0-6.5 | KERRIA | 6.0-7.0 | RHODODENDREN | 5.0-6.0 |
| DAHLIA | 6.0-7.5 | LABURNUM | 6.0-7.0 | ROSES | 6.0-7.0 |
| DAY LILY | 6.0-8.0 | LAUREL | 6.5-7.5 | HYBRID TEA | 6.5-7.0 |
| DELPHINIUM | 6.0-7.5 | LAVENDER | 6.5-7.5 | CLIMBING | 6.0-7.0 |
| DEUTZIA | 6.0-7.5 | LIATRIS | 5.5-7.5 | RAMBLING | 5.5-7.0 |
| DIANTHUS | 6.0-7.5 | LIGUSTRUM | 5.0-7.5 | SALVIA | 5.0-7.5 |
| DOGWOOD | 5.0-7.0 | LILAC | 6.0-7.5 | SCABIOSA | 6.0-7.5 |
| EDELWEISS | 6.5-7.5 | LILY OF THE VALLEY | 4.5-6.0 | SEDUM | 5.0-7.0 |
| ELAEAGNUS | 5.0-7.5 | LITHOSPERMUM | 5.0-6.5 | SNAPDRAGON | 6.0-7.5 |
| ENKIANTHUS | 5.0-6.0 | LOBELIA | 6.5-7.5 | SNOWDROP | 5.5-7.0 |
| ERICA | 4.5-6.0 | LUPINUS | 5.5-7.0 | SOAPWORT | 6.0-8.0 |
| EUPHORBIA | 6.0-8.0 | MAGNOLIA | 5.0-6.5 | SPEEDWELL | 6.07.5 |
| EVERLASTINGS | 5.0-6.0 | MAHONIA | 5.0-7.0 | SPIRAEA | 5.5-6.5 |
| FIRETHORN | 6.0-8.0 | MARIGOLD | 6.0-7.0 | SPRUCE | 6.0-7.0 |
| FORGET-ME-NOTS | 6.0-7.0 | MOLINIA | 4.0-6.0 | STOCK | 4.0-5.0 |
| FORSYTHIA | 6.0-8.0 | MORAEA | 5.5-6.5 | STONECROP | 6.0-7.5 |
| FOXGLOVE | 6.0-7.5 | MORNING GLORY | 6.0-7.5 | SUMACK | 6.5-6.5 |
| FRITILLARIA | 6.0-8.0 | MOSS | 4.0-5.0 | SUNFLOWER | 5.0-7.0 |
| FUCHSIA | 5.5-7.5 | MOSS, SPHAGNUM | 3.5-5.0 | SWEET PEA | 6.0-8.0 |
| GAILLARDIA | 6.0-7.0 | MYOSOTIS | 6.0-7.0 | SWEET WILLIAM | 6.0-7.5 |
| GAZANIA | 6.0-8.0 | NARCISSUS | 5.0-7.5 | TAMARIX | 6.0-8.0 |
| GENTIANA | 5.5-7.0 | NASTURTIUM | 5.5-7.5 | TRILLIUM | 6.5-8.0 |
| GEUM | 6.0-7.5 | NICOTIANA | 5.5-6.5 | TULIP | 6.0-7.0 |
| GLADIOLI | 6.0-7.0 | PACHYSANDRA | 5.0-8.0 | VIBERNUM | 5.0-7.5 |
| | | | | VIOLA | 5.5-6.5 |

| NAME | pH |
|---|---|
| VIRGINIA CREEPER | 6.0-7.5 |
| WALLFLOWER | 5.5-7.0 |
| WATER LILY | 5.5-6.5 |
| WEIGELIA | 6.0-7.5 |
| WISTARIA | 6.0-8.0 |
| ZINNIA | 5.5-7.5 |
| TURF & ORNAMENTAL GRASSES | |
| BAHAI | 6.5-7.5 |
| BENT | 5.5-6.5 |
| BERMUDA | 6.0-7.0 |
| CANADA BLUE | 4.5-8.4 |
| CLOVER | 6.0-7.0 |
| KENTUCKY BLUE | 6.0-7.5 |
| MEADOW | 6.0-7.5 |
| PAMPAS | 6.0-8.0 |
| RED TOP | 6.0-6.5 |
| RYE | 6.0-7.0 |
| ST. AUGUSTINE | 6.5-7.5 |
| TALL FESCUE | 6.0-7.0 |
| VELVET BENT | 5.0-6.0 |
| ZOYSIA | 6.0-7.0 |

FIG. 7C

ADJUSTING SOIL pH - HOW MUCH TO APPLY

| Material | pH Change | Sandy | Loamy | Clay |
|---|---|---|---|---|
| Dolomitic or calcic limestone | +0.5 unit (0.5 pH) | 2.5 | 5.0 | 5.5 |
|  | +1.0 unit (1.0 pH) | 5.0 | 8.5 | 11.0 |
| Hydrated Lime | +0.5 unit (0.5 pH) | 1.5 - 2.0 | 3 - 4 | 4.0 - 4.5 |
|  | +1.0 unit (1.0 pH) | 3.5 - 4.0 | 6.0 - 6.5 | 8.0 - 8.5 |
| Iron Sulfate | -0.5 unit (0.5 pH) | 0.75 | 1.5 | 2.0 |
|  | -1.0 unit (1.0 pH) | 1.5 | 3.0 | 4.0 |
| Aluminum Sulfate | -0.5 unit (0.5 pH) | 0.5 - 0.75 | 1 - 1.25 | 1.5 |
|  | -1.0 unit (1.0 pH) | 1 - 1.25 | 2.25 | 3.0 |

Amounts listed are pounds per 100 square feet. Do not add more than 5lbs. of lime or sulfur in one application.

FIG. 8

FEEDING PRIOR TO PLANTING

Adequate reserves of plant food should be available in the soil before planting vegetables, preparing a seed or flower bed, sodding or seeding a lawn, or planting shrubs and trees. To make up any deficiencies, apply fertilizers from the following chart according to your soil test result.

| TEST RESULTS | (0) Depleted | (1) Deficient | (2) Adequate | (3 & 4) Surplus / Sufficient |
|---|---|---|---|---|
| Nitrogen Fertilizers (%N) | | | | |
| Dried Blood (11%) | 36 | 19 | 6 | N/A |
| Nitrate of Soda (16%) | 27 | 14 | 3 | N/A |
| Phosphate Fertilizers (%P) | | | | |
| Bone Meal (19%) | 27 | 14 | 6 | N/A |
| Triple Superphosphate (46%) | 10.25 | 5.25-5.5 | 2.25 | N/A |
| Potash Fertilizers (%K) | | | | |
| Muriate of Potash (60%) | 8.75 - 9 | 4.75-5 | 2.25-2.5 | N/A |

Amounts listed are ounces per 100 square feet. (Ounces referred to are by weight)

FIG. 9

RECOMMENDATIONS FOR N, P AND K RESULTS

| | Very Low | | | Low | | | Medium | | | High | | |
|---|---|---|---|---|---|---|---|---|---|---|---|---|
| | N | P | K | N | P | K | N | P | K | N | P | K |
| Lawn | 22.0-22.5 | 0.75-1.0 | 4.75-5.0 | 14.0-14.5 | 1.0-1.5 | 2.25-2.5 | 3.75-4.0 | 0 | 0 | N/A | N/A | N/A |
| Fruit | 14.0-14.5 | 6.5 | 13.5-14.0 | 7.75-8.0 | 4.0-4.25 | 8.75-9.0 | 3.75-4.0 | 2.25 | 4.75-5.0 | N/A | N/A | N/A |
| Flower | 14.0-14.25 | 6.5 | 13.5-14.0 | 7.75-8.0 | 4.0-4.25 | 8.75-9.0 | 3.75-4.0 | 2.25 | 4.75-5.0 | N/A | N/A | N/A |
| Shrubs (flowering) | 14.0-14.25 | 8.25-8.5 | 8.75-9.0 | 7.75-8.0 | 4.0-4.25 | 8.75-9.0 | 3.75-4.0 | 1.0-1.25 | 4.75-5.0 | N/A | N/A | N/A |
| Shrubs (foliage) | 22.0-22.5 | 10.5-10.75 | 8.75-9.0 | 14.0-14.5 | 5.25-5.5 | 4.75-5.0 | 3.75-4.0 | 2.25 | 2.25-2.5 | N/A | N/A | N/A |
| Veggies (root) | 14.0-14.25 | 12.0-12.25 | 8.75-9.0 | 14.0-14.5 | 5.25-5.5 | 4.75-5.0 | 3.75-4.0 | 3.0 | 2.25-2.5 | N/A | N/A | N/A |
| Veggies (leafy) | 28.25-29.0 | 10.25 | 8.75-9.0 | 14.0-14.5 | 5.25-5.5 | 4.75-5.0 | 7.75-8.0 | 2.25 | 2.25-2.5 | N/A | N/A | N/A |
| Tree | 14.0-14.5 | 10.25 | 8.75-9.0 | 7.75-8.0 | 4.0-4.25 | 4.75-5.0 | 3.75-4.0 | 2.25 | 2.25-2.5 | N/A | N/A | N/A |
| General Feed | 22.0-22.5 | 8.25-8.5 | 8.75-9.0 | 10.5-11.0 | 4.0-4.25 | 4.75-5.0 | 3.75-4.0 | 1.0-1.25 | 2.25-2.5 | N/A | N/A | N/A |

The recommendations are based on the following fertilizers sources: Nitrate of Soda (16% N), Triple Superphosphate (45% $P_2O_5$) and Muriate of Potash (60% $K_2O$). The amounts listed are in oz./100 sq. ft. (Ounces referred to are by weight, not volume.) If you wish to use other fertilizer, simply check the packages for the percentage of nutrients for N,P,&K and adjust the application level accordingly.

FIG. 10

SPECIAL RECOMMENDATIONS FOR LAWNS

| Fertilizer Type | (0&1) Depleted | (2) Deficient | (3) Adequate sufficient | (4) Surplus or |
|---|---|---|---|---|
| 24-4-4 | 4.0 lbs | 2.0 lbs. | 1.0 lb. | N/A |
| 24-3-4 | 3.1 lbs | 1.55 lbs | .77 lbs | N/A |
| 30-4-4 | 3.0 lbs | 1.5 lbs | .75 lbs | N/A |

Amounts listed are pounds per 1000 square feet

FIG. 11

SOIL TESTING SYSTEMS AND METHODS THEREOF

CROSS-REFERENCE TO RELATED APPLICATION

The present application claims the benefit of and priority to U.S. Provisional Patent Application No. 61/819,873, filed on May 6, 2013, the entire contents of which are incorporated by reference herein.

FIELD OF THE DISCLOSURE

The present disclosure relates to soil testing systems and methods thereof.

BRIEF DESCRIPTION OF THE DRAWINGS

The features and advantages of the present disclosure will be more fully understood with reference to the following, detailed description of an illustrative embodiment of the present disclosure when taken in conjunction with the accompanying figures, wherein:

FIG. 7A is a reference table providing suggested soil pH values associated with various types of vegetation;

FIG. 7B is a reference table providing suggested soil pH values associated with various types of vegetation continued from FIG. 7A;

FIG. 7C is a reference table providing suggested soil pH values associated with various types of vegetation continued from FIG. 7B;

FIG. 8 is a reference table providing suggested soil pH values associated with corresponding soil nutrient values;

FIG. 9 is a reference table providing suggested levels of soil additives to adjust soil pH values;

FIG. 10 is a reference table providing suggested levels of soil additives to adjust soil nutrient values; and FIG. 11 is a reference table providing suggested levels of soil additives to adjust soil nutrient values in specific applications.

SUMMARY

Figure 1A:
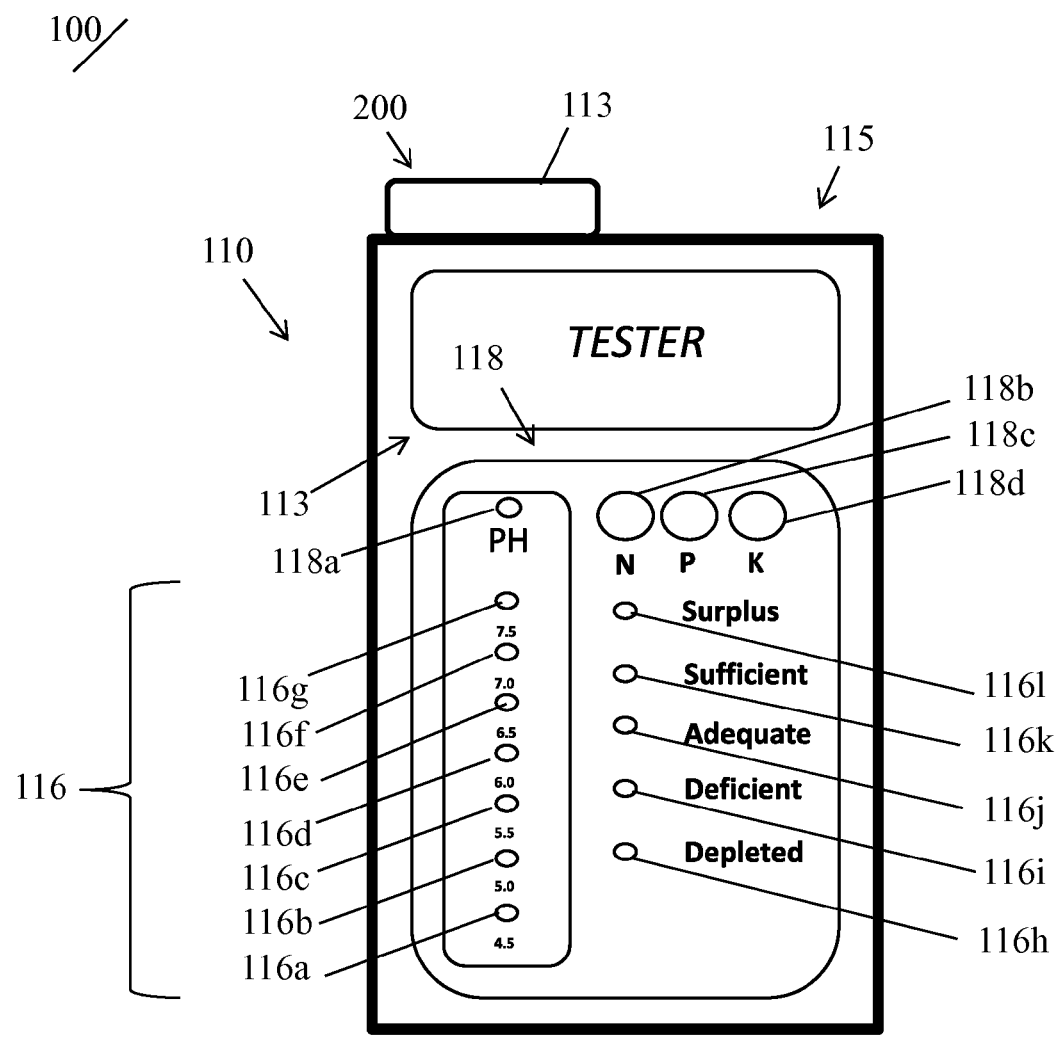
FIG. 1A is a front view of a soil testing system according to an exemplary embodiment of the present disclosure.

A soil tester is disclosed, and comprises a housing and a sampling apparatus. The housing includes an interior sampling chamber configured to receive a sample container. The sampling apparatus comprises a photodetector and a light source. The photodetector is mounted along a portion of the interior sampling chamber and has a variable resistance determined by a property of incident light. The light source is mounted to the interior sampling chamber in a transmissive orientation relative to the photodetector so that a beam of light can be transmitted from the light source to the photodetector through the interior sampling chamber. A display on the housing is responsive to the photodetector.

In an exemplary embodiment, the sample container is configured to retain a solution configured to change an optical property of the beam of light passing through it.

In an exemplary embodiment, the optical property is an amplitude of the beam of light.

In an exemplary embodiment, the optical property is the wavelength of the transmitted beam of light;

In an exemplary embodiment, the variable resistance of the photodetector is associated with a known chemical property of a solution retained in the sample container.

In an exemplary embodiment, the known chemical property is a pH level of a portion of the solution.

In an exemplary embodiment, the known chemical property is an amount of nitrate of a portion of the solution.

In an exemplary embodiment, the known chemical property is an amount of phosphoric acid of a portion of the solution.

In an exemplary embodiment, the known chemical property is an amount of potash of a portion of the solution.

According to an exemplary embodiment of the present disclosure, a soil testing system is disclosed, and comprises: a soil tester, a sample container, and a display. The soil tester comprises a housing including an interior sampling chamber and a sampling apparatus comprising a photodetector and a light source. The photodetector is mounted along a portion of the interior sampling chamber and having a variable resistance determined by a property of incident light. The light source is mounted to the interior sampling chamber in a transmissive orientation to the photodetector so that a beam of light can be transmitted from the light source to the photodetector through the interior sampling chamber. The sample container comprises a soil sample, a reagent, and a liquid so that the soil sample, the reagent, and the liquid form a solution in the sample container. The display on the housing is responsive to the photodetector.

In an exemplary embodiment, the solution has a distinct optical property determined at least by the soil sample solution.

In an exemplary embodiment, the distinct optical property is the wavelength of the solution.

In an exemplary embodiment, the variable resistance of the photodetector is determined by the distinct optical property of the soil sample solution.

In an exemplary embodiment, the variable resistance of the photodetector corresponds to a known chemical property of the soil sample solution.

In an exemplary embodiment, the known chemical property is a pH level of the soil sample.

In an exemplary embodiment, the known chemical property is an amount of nitrate of the soil sample.

In an exemplary embodiment, the known chemical property is an amount of phosphoric acid of the soil sample.

In an exemplary embodiment, the known chemical property is an amount of potash of the soil sample.

According to an exemplary embodiment of the present disclosure, a method of testing a soil sample comprises: providing a soil tester that comprises a housing including an interior sampling chamber, the soil tester also comprises a sampling apparatus that includes a photodetector mounted along a portion of the interior sampling chamber and having a variable resistance determined by a property of incident light and a light source mounted to the interior sampling chamber in transmissive orientation to the photodetector; providing a sample container; providing a reagent; providing a soil sample; combining the soil sample and reagent in the sample container so that a solution is formed; inserting the sample container into the interior sampling chamber of the soil tester; activating the at least one light source; passing at least a portion of the light through the combined mixture and measuring the property of the light passing through the combined mixtures; comparing the parameters of the light to values in a lookup table and displaying the test results on a display.

In exemplary embodiments, the reagent can be a liquid.

DETAILED DESCRIPTION

The disclosure generally relates to an apparatus for testing the chemical properties of a sample substance through photodetection and associated methods of use. Specifically, in exemplary embodiments a soil tester is disclosed that is configured to determine an amount of one or more chemicals, for example, fertilizing chemicals such as nitrates ($NO_3$), phosphoric acid ($P_2O_5$), and potash (potassium oxide [$K_2O$]), to name a few, that are present in soil. Additionally or alternatively, a soil tester as disclosed in exemplary embodiments herein is configured to measure the pH (e.g., acidity or alkalinity level) of soil. Specifically, soil testers according to exemplary embodiments herein are configured to determine an amount of one or more fertilizing chemicals and/or pH of the soil sample through the measurement of the color, diffusivity or transmissibility of light through a solution containing a soil sample placed in the soil tester.

In exemplary embodiments, soil samples may be dissolved in liquid with a reagent such that the resulting solution has distinct optical properties. Alternatively, the reagent may be a liquid and the reagent liquid is mixed with the soil sample. A beam of light having known optical properties, for example, frequency, wavelength, and/or amplitude, can be transmitted through the solution and analyzed thereafter such that a changed optical property of the beam of light can be used to determine a corresponding chemical property of the soil in the solution. In embodiments, such properties may include the quantity of fertilizing chemicals and/or the pH of the soil sample. Such information can be relayed to a user through a simplified user interface that indicates results on a relative or otherwise easily-understandable scale (e.g., textual language indicating sample is "adequate", simple number scales, etc.) for each test rather than complex exact results (e.g., parts per million).

In exemplary embodiments, the systems and methods disclosed herein can be used for a variety of chemical analysis purposes in addition to or alternative to soil testing, for example, water testing, testing of aqueous solutions, testing of swimming pool water, testing of hot tub water, testing for other chemicals in soil or other solutions such as, but not limited to copper, iron, zinc, and heavy metals, to name a few, and/or testing of any other solution.

Figure 1B:
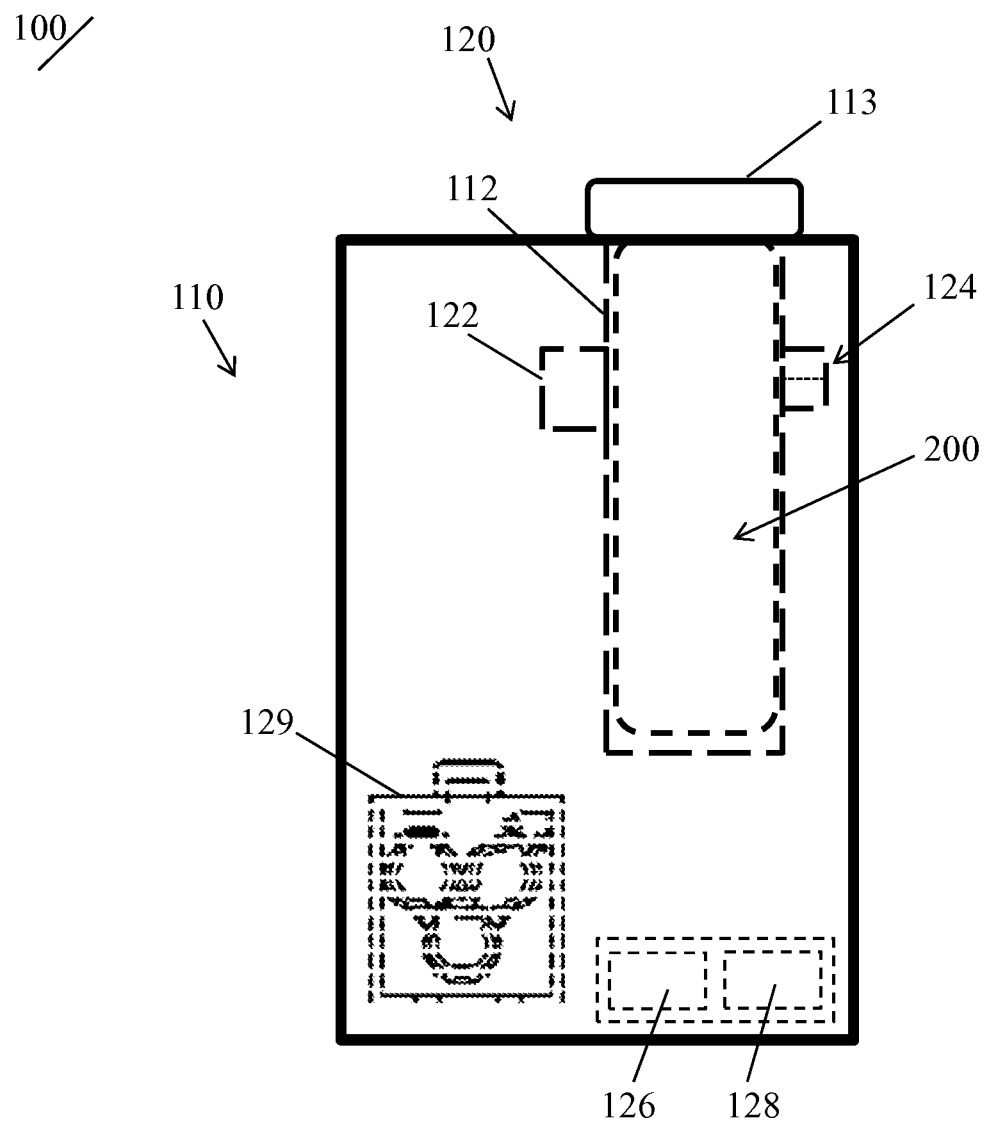
FIG. 1B is a rear view of the soil testing system of FIG. 1A.

Referring initially to FIGS. 1A and 1B, a soil testing system according to an exemplary embodiment is disclosed, and generally designated 1000. Soil testing system 1000 comprises a soil tester 100 and at least one test sample 200 for use with soil tester 100. Soil tester 100 comprises a housing 110 defining an interior sampling chamber 112 and including an outward-facing display portion 115, and a sampling apparatus 120 configured to detect one or more properties of a test sample 200 stored in a sample container 114.

As described above, soil tester 100 is configured to test one or more properties of test sample 200 via detection of the properties of light passing through the test sample 200. Accordingly, sampling apparatus 120 comprises at least one light source 122, and a photodetector 124. In embodiments, a microcontroller 126, and, optionally, an integrated or separate analog-to-digital converter 128 may be included in soil tester 100. A power source 129, for example, one or more chemical batteries may be provided to supply power to the sampling apparatus 120. In embodiments, power source 129 may have a different configuration, for example, a capacitor or inductor.

As shown, light source 122 is mounted to an outer portion of interior sampling chamber 112 so that light can be transmitted from light source 122 to photodetector 124, also mounted on the interior sampling chamber 112. Light source 122 and photodetector 124 may be mounted in diametrical opposition, as shown. In embodiments, light source 122 and photodetector 124 may have a different arrangement, e.g., a diametrically offset arrangement, and incorporate structure to facilitate the transmission of light therebetween, for example, a pivotable beam emitter or reflector.

Light source 122 comprises a light source capable of producing multiple wavelengths of light associated with different colors in the visible light spectrum, for example, red, blue, green, and/or yellow, to name a few. In embodiments, the light source 122 may be configured to produce wavelengths of light associated with colors outside of the visible light spectrum, for example ultraviolet (UV) or infrared (IR). In embodiments, light source 122 may have the form of a multi-colored light bulb, a multi-colored LED (light emitting diode), and/or multi-colored laser diode. It will be understood that a multi-colored light source may be a single source of light capable of producing multiple wavelengths of light, or may be a combination of single color and/or multi-colored light sources, for example, a bi-color LED or tri-color LED.

In the exemplary embodiment shown, light source 122 is a bi-color LED with a red diode 122a and a green-colored diode 122b. Light source 122 may be a WP57EGW dual R/G LED (available from Kingbright). Those skilled in the art may envision other suitable components for use as light source 122. Photodetector 124 may comprise a light sensor, for example, a Cadmium Sulfide (CdS) photocell, a charge-coupled device (ccd), a complementary metal oxide semiconductor (CMOS) or CdS photo sensitive variable resistor, to name a few, or other known sensors that are capable of detecting and/or distinguishing different properties of incident light. Specifically, photodetector 124 is configured to provide a variable electrical resistance along a circuit path within soil tester 100 that is dependent upon at least the intensity (amplitude) of beam of light incident to the photodetector 124. Accordingly, beams of light having different optical properties that strike photodetector 124 cause the electrical resistance of photodetector 124 to change according to the properties of the respective beam of light, e.g., the intensity of the incident beam of light. Photodetector 124 may be electrically coupled with microcontroller 126 and analog to digital converter 128 so that photodetector 124 can produce one or more digital signals upon detecting a source of light. In the exemplary embodiment shown, photodetector 124 may be placed in series with an electrical impedance having a known resistance, e.g., a 10 kΩ resistor, so that microcontroller 126 can measure the potential difference across the known resistor and the photodetector 124 to determine the resistance of the photodetector 124.

Figure 5:
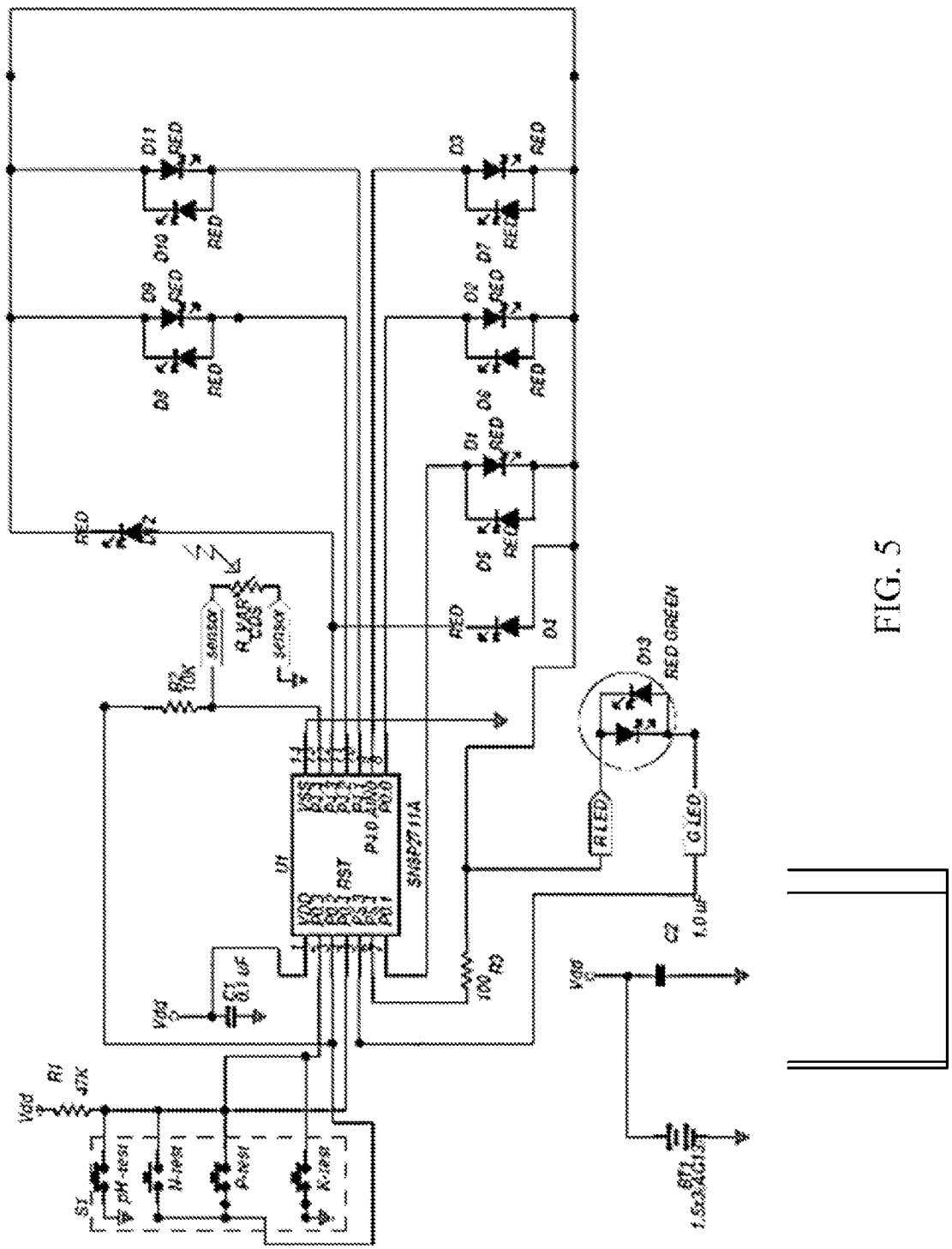
FIG. 5 is a schematic diagram of the electrical components of the soil testing system of FIG. 1A according to an exemplary embodiment of the present disclosure.

Referring momentarily to FIG. 5, a circuit diagram of soil tester 100 according to an exemplary embodiment of the present disclosure is illustrated. It will be understood that soil tester 100 may have a different configuration suitable for its intended purpose.

Referring again to FIGS. 1A and 1B, display portion 115 of the housing 110 of soil tester 100 includes a plurality of indicators 116 and/or user inputs 118 associated with sampling processes of soil tester 100. In the exemplary embodiment shown, display portion 115 includes numerical indicators 116a, 116b, 116c, 116d, 116e, 116f, and 116g corresponding respectively to pH values of 4.5, 5.0, 5.5, 6.0, 6.5, 7.0, and 7.5 of test sample 200. Indicators 116 may be comprised of lights located near corresponding indicia on display portion 115, as shown, or in embodiments may have a different configuration, such as a digital display or analog gauge. Further, display portion 115 includes a pH test input 118a, a nitrate test input 118b, a phosphoric acid test input 118c, and a potash test input 118d. Inputs 118 may be tactile buttons located on display portion 115, as shown, that initiate one or more processes of soil tester 100, as described further herein. In embodiments, inputs 118 may have a different configuration, for example, capacitive buttons, knobs, switches, or toggles, to name a few. In embodiments, display portion 115 may have a different configuration, e.g., one or more digital and/or analog readouts. In exemplary embodiments, insertion of sample container 114 into soil tester 100 may cause activation of a process thereof, for example, by depressing a recessed button within interior sampling chamber 112 or completing an electrical circuit.

Figure 2A:
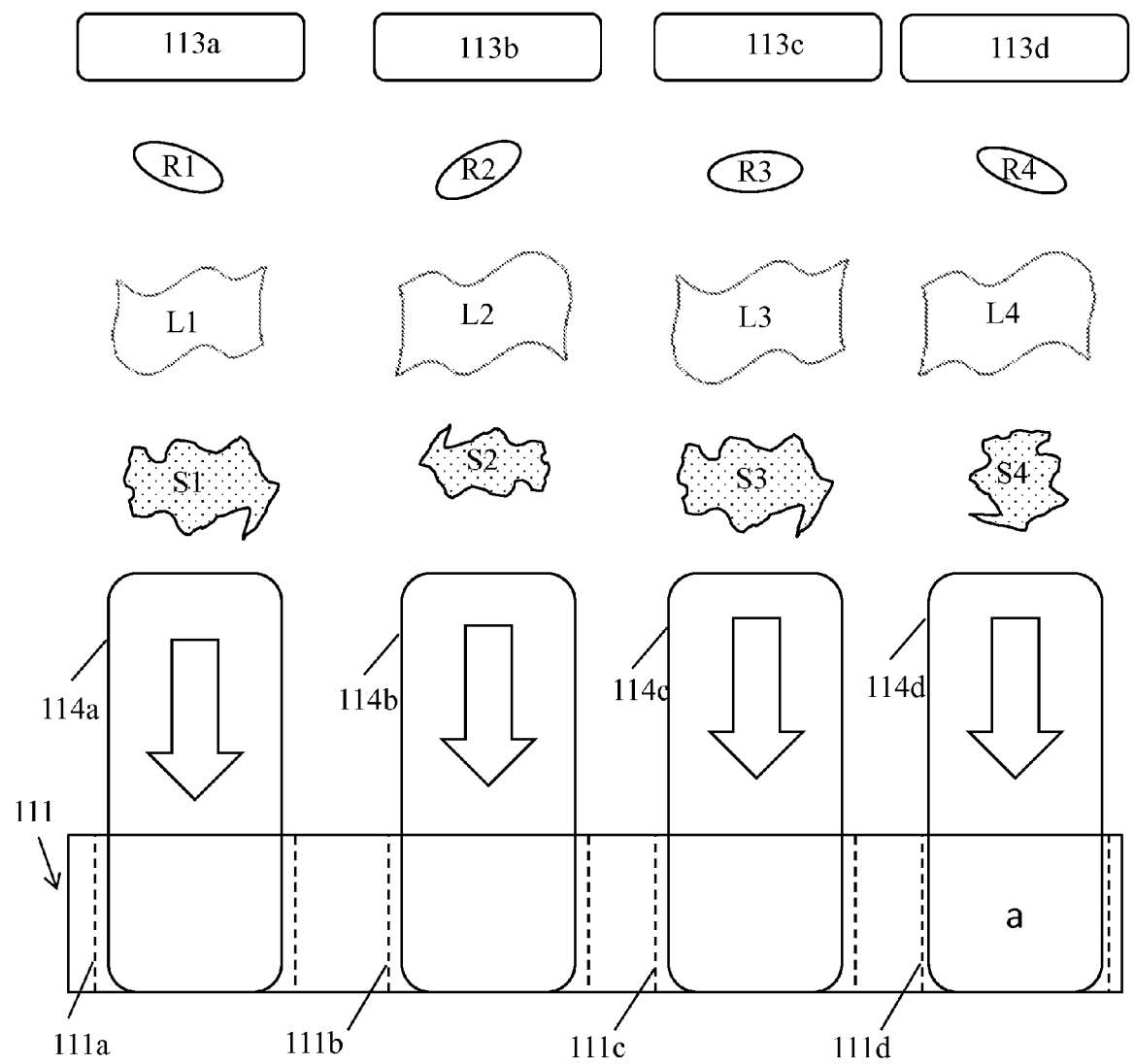
FIG. 2A is a first sequential view of a preparation of a plurality of test samples for use with the soil tester of the soil testing system of FIG. 1A.
Figure 2B:
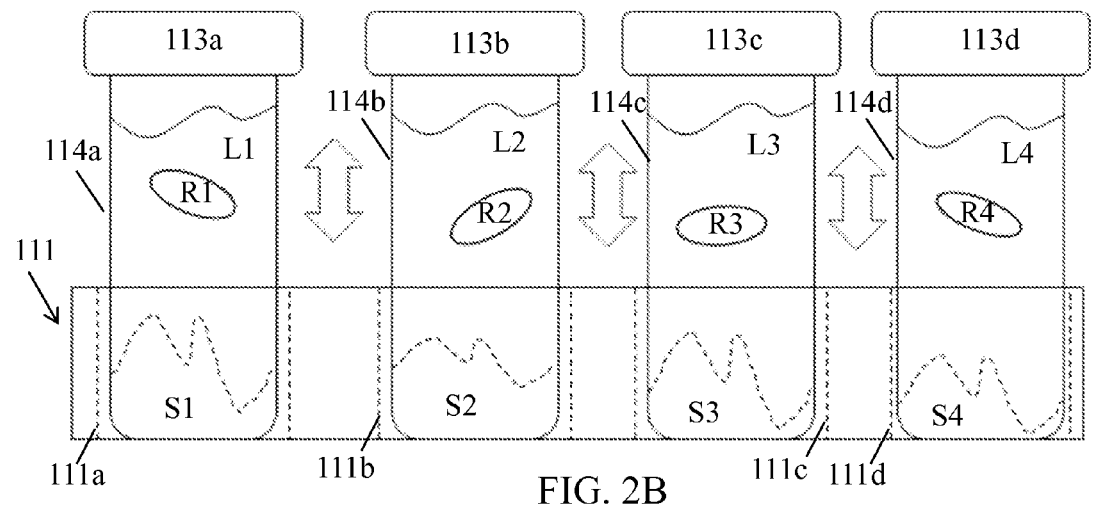
FIG. 2B is a second sequential view of a preparation of a plurality of test samples for use with the soil tester of the soil testing system of FIG. 1A.
Figure 2C:
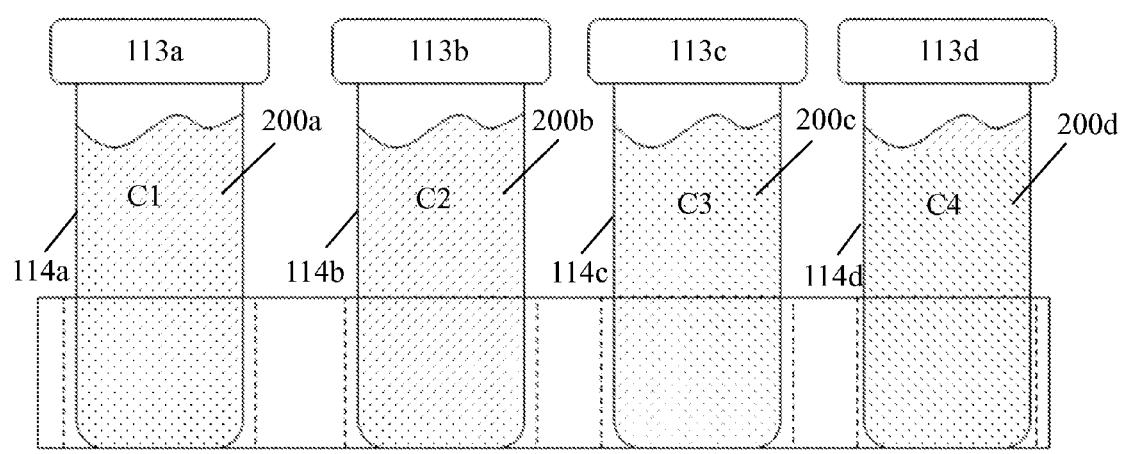
FIG. 2C is a third sequential view of a preparation of a plurality of test samples for use with the soil tester of the soil testing system of FIG. 1A.

Turning now to FIGS. 2A, 2B, and 2C, preparation of test samples for use with soil tester 100 is illustrated according to an exemplary embodiment of the present disclosure. As shown, the preparation of four sample containers 114a, 114b, 114c, 114d is illustrated. In embodiments, a single sample container may be used with soil tester 100, or any plurality of sample containers, for example, 2, 3, 4, 5, 6, 7, or 8, to name a few. In the exemplary embodiment shown, a base 111 is provided with apertures 111a, 111b, 111c, 111d so that corresponding sample containers 114a, 114b, 114c, 114d can be inserted into the base 111 and maintained in a substantially upright position.

Still referring to FIG. 2A, each sample container 114a, 114b, 114c, and 114d is configured to receive and retain a respective liquid L1, L2, L3, L4 along with a corresponding soil sample S1, S2, S3, S4 and reagent R1, R2, R3, R4. In embodiments, one or more of a liquid, solution, and/or reagent may be specific to a particular sample container and/or to each other.

Liquid L1, L2, L3, L4 may be water, or another type of testing liquid such as methyl blue. Liquid L1, L2, L3, L4 may be a non-viscous substance conducive to the dissolution of solid components therein, as will be described further below.

Soil samples S1, S2, S3, and S4 are physical samples from a location that is desired to be analyzed with soil tester 100, for example, a farm, lawn, or garden. Accordingly, soil samples may be taken from topsoil or deeper portions of a soil environment, for example, a depth proximate deeper-growing vegetation such as roots or tubers.

Reagents R1, R2, R3, and R4 are compounds configured to react with a soil sample in the presence of a liquid such as water such that an optical property, such as color, of the resulting reagent, soil, and liquid solution is indicative of a chemical property of the soil. Each of reagents R1, R2, R3, R4 may be contained within a capsule, as shown, or may be provided in another liquid or solid form, such as a powder. In the exemplary embodiment shown, the capsule each reagent R1, R2, R3, R4 may be opened by a user so that a powdered form of the reagent within can be added to a respective sample container. In embodiments, a color of a capsule may correspond to a color of a user input 118 on display portion 115.

Reagents R1, R2, R3, and R4 can be in liquid form eliminating the need to add water or other liquids or can be provided in multiple components requiring mixing to be appropriate for testing different attributes.

Each of reagents R1, R2, R3, R4 is formulated to cause a change of an optical property of the solution to which it is added, for example, color, cloudiness, opacity, and/or clarity, to name a few, within a predetermined range to indicate the relative presence of a tested substance, such as phosphoric acid, nitrate, potash, or the relative acidic, neutral, or basic characteristics (pH) thereof. Accordingly, each reagent R1, R2, R3, R4 may have an indicia, for example, a color of the respective capsule, corresponding to one of a measurement test for one of phosphoric acid, nitrate, potash, and pH.

In exemplary embodiments, a reagent formulated to react with nitrates may be comprised of: lactose monohydrate, tartaric acid, manganese sulphate, sulfanilic acid, N.I. napthylethylene diamine dihydrochloride, zinc metal powder, and magnesium stearate, to name a few.

In exemplary embodiments, a reagent formulated to react with phosphoric acid may be comprised of: sodium sulphate, anhydrous potassium hydrogen sulphate, ascorbic acid, ammonium molybdate, and magnesium stearate, to name a few.

In exemplary embodiments, a reagent formulated to react with potash may be comprised of: lactose monohydrate, bismark brown R, sodium tetraphenylborate, and magnesium stearate, to name a few.

In exemplary embodiments, a reagent formulated to react in a manner indicative of the pH of the surrounding environment may be comprised of: barium sulfate, methyl red, and bromothymol blue, to name a few.

As shown, sample containers 114a, 114b, 114c, 114d are provided with a respective lid 113a, 113b, 113c, 113d configured to fit over the open top portion of the respective sample containers. Accordingly, sample containers 114a, 114b, 114c, 114d may be selectively opened and closed, for example, to allow the insertion of soil samples, reagents, and liquids, and closed thereafter to retain the contents of the sample containers.

Turning now to FIGS. 2B and 2C, 114a, 114b, 114c, 114d are shown enclosed by respective lids 113a, 113b, 113c, 113d and containing respective liquids L1, L2, L3, L4, soil samples S1, S2, S3, S4, and reagents R1, R2, R3, R4. A user may then shake, stir, or otherwise impart motion to the sample containers 114a, 114b, 114c, 114d, either separately or in concert, for example, within base 111, so that the contents of each sample container 114a, 114b, 114c, 114d are substantially transformed into respective test samples 200a, 200b, 200c, 200d comprising a solution via dissolution or dissipation of the respective soil samples and reagents into the liquids. Each sample container 114a, 114b, 114c, 114d will contain a resultant solution with a color C1, C2, C3, C4 or transmissibility determined by the contents of the respective liquid, soil sample, and reagent dissolved therein. In embodiments, one or more of test samples 200a, 200b, 200c, 200d may have a similar or identical color, or may have different colors or transmissibility.

Figure 3:
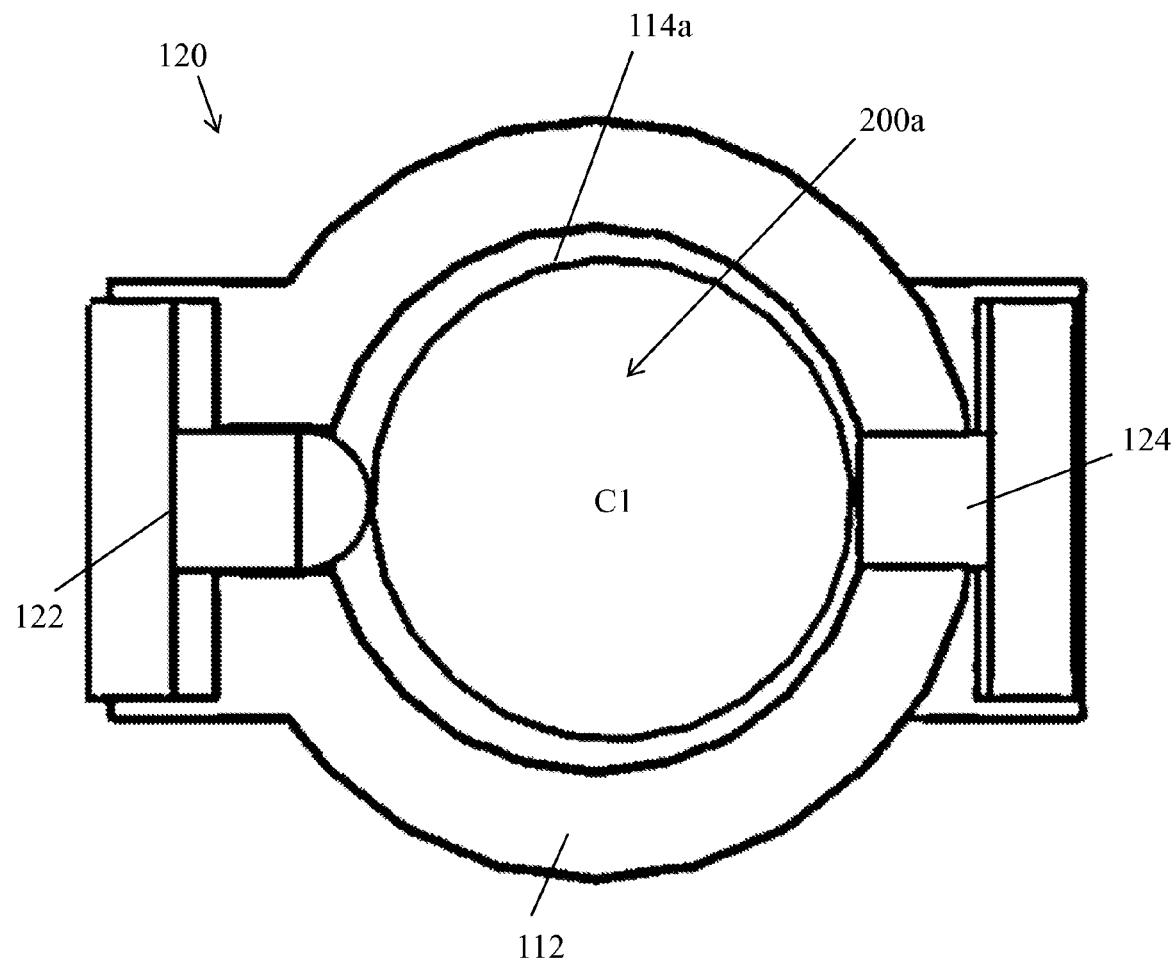
FIG. 3 is a top plan view of the sampling apparatus of the soil testing system of FIG. 1A.

Turning now to FIG. 3 a top view of the interior sampling chamber 112 of soil tester 100 is shown, with sampling container 114a having a test sample 200a comprised of a solution with color C1 inserted therein after dissolving the soil sample S1 and reagent R1 into liquid L1 (see FIGS. 4A, 4B, 4C). As shown, sampling container 114a is positioned within interior sampling chamber 112 such that the solution with color C1 is positioned along a direct line between the light source 122 and photodetector 124. In embodiments, light source 122 and/or photodetector 124 may be positioned toward the top portion of interior sampling chamber 112, for example, approximately ⅔ vertically along the height of interior sampling chamber 112, so that they are positioned sufficiently vertically so as not to be affected by potential settling of settled or otherwise non-dissolved components of the solution in sample container 114a.

Figure 4:
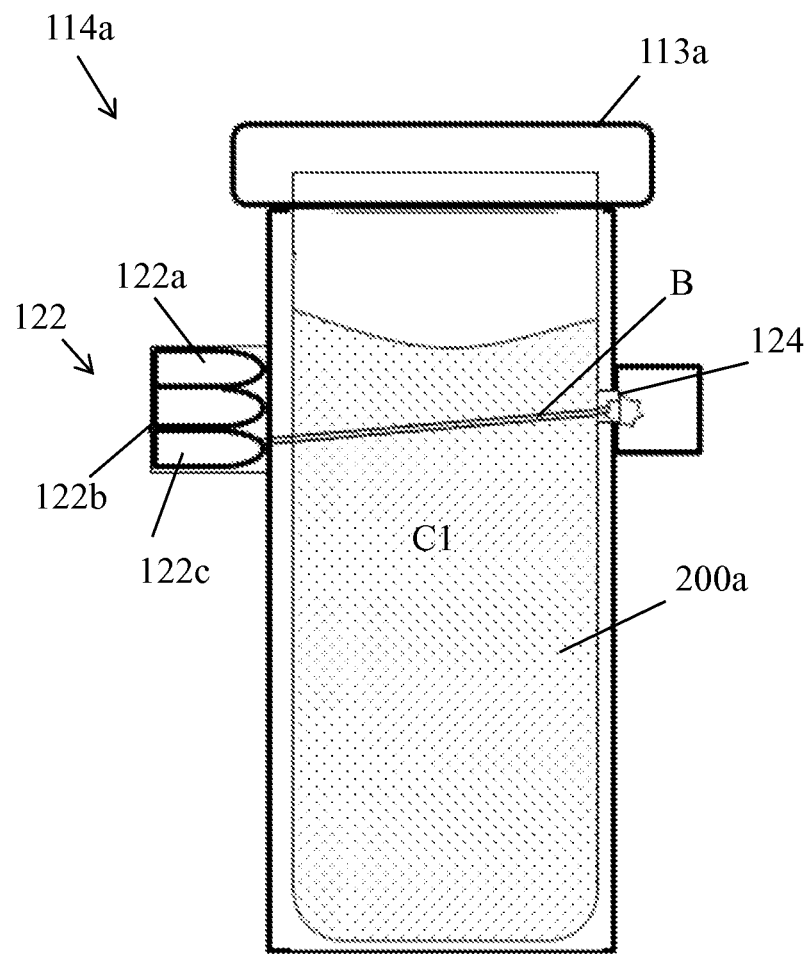
FIG. 4 is a front view of the sampling apparatus of the soil testing system of FIG. 1A during use.

Turning to FIG. 4, a section view of the sampling apparatus 120 is shown in operation. A user may activate a modality of soil tester 100 by activating one of user inputs 118 to activate light source 122. In this manner, light source 122 can be activated in a particular mode corresponding to one of a pH test, nitrate test, phosphoric acid test, potash test, or other similar test.

Upon activation of at least one component of light source 122, at least one beam B of light is transmitted through sample container 114 toward photodetector 124. Accordingly, sample container 114 is formed of an at least partially transparent material, for example, plastic or glass, configured to allow light to pass therethrough. As the beam B of light passes through sample container 114 and the solution having color C1 therein, one or more optical properties of the beam B of light may be changed, for example, amplitude, so that a changed intensity of the beam B of light is received by the photodetector 124 after passage through the sample container 114.

In this manner, the color intensity of the solution in the sample container 114 may serve as a filter to facilitate the passage of one or more wavelengths (colors) of light and to facilitate the passage of one or more wavelengths of light therethrough. For example, a red-colored solution may facilitate the passage of a red-colored beam of light therethrough, but may substantially inhibit the passage of green-colored light therethrough, and vice-versa. As described above, photodetector 124 is configured to detect the intensity of a given color of light for multiple different wavelengths of light, such that photodetector 124 is configured to determine one or more optical properties of incident light across multiple color-dependent tests.

In the exemplary embodiment shown, a user designates the behavior of light source 122 via actuating one or more of user inputs 118a, 118b, 118c, 118d. In this manner, a known property of a soil sample is designated as the test factor by the user. Accordingly, a test for the presence of a chemical in a soil sample may comprise the activation of only one light, or in embodiments, multiple single lights activated in sequence, in order to conduct the test.

In embodiments, soil tester 100 may be configured to detect not only the relative presence of a chemical in a soil sample, but also which chemical is desirably the subject of the test. For example, in the absence of separate user inputs 118a, 118b, 118c, 118d to designate a chemical that is the subject of the test, soil tester 100 may activate light source 122 and use the variable resistance of photodetector 124 to determine if the chemical property of each of nitrates, phosphoric acid, potash, and pH falls within acceptable ranges of the one or more reference tables for that specific chemical. In embodiments, only one of the four chemical tests will fall within a range for a given soil sample, which allows the soil tester to determine the target chemical and relative amount thereof without receiving an instruction via a user input.

In embodiments, more than one chemical test may fall within an accepted range for a given soil sample, representing multiple variables to be determined by the soil tester 100. Accordingly, the light source 122 within soil tester 100 may incorporate lights of multiple different colors, for example, red, blue, green, and/or yellow, to name a few, that may be initiated in sequence so that soil tester 100 initiates multiple independent tests of a soil sample in order to resolve the multiple variables of which chemical is subject of the test and the relative amount of said chemical.

Figure 6:
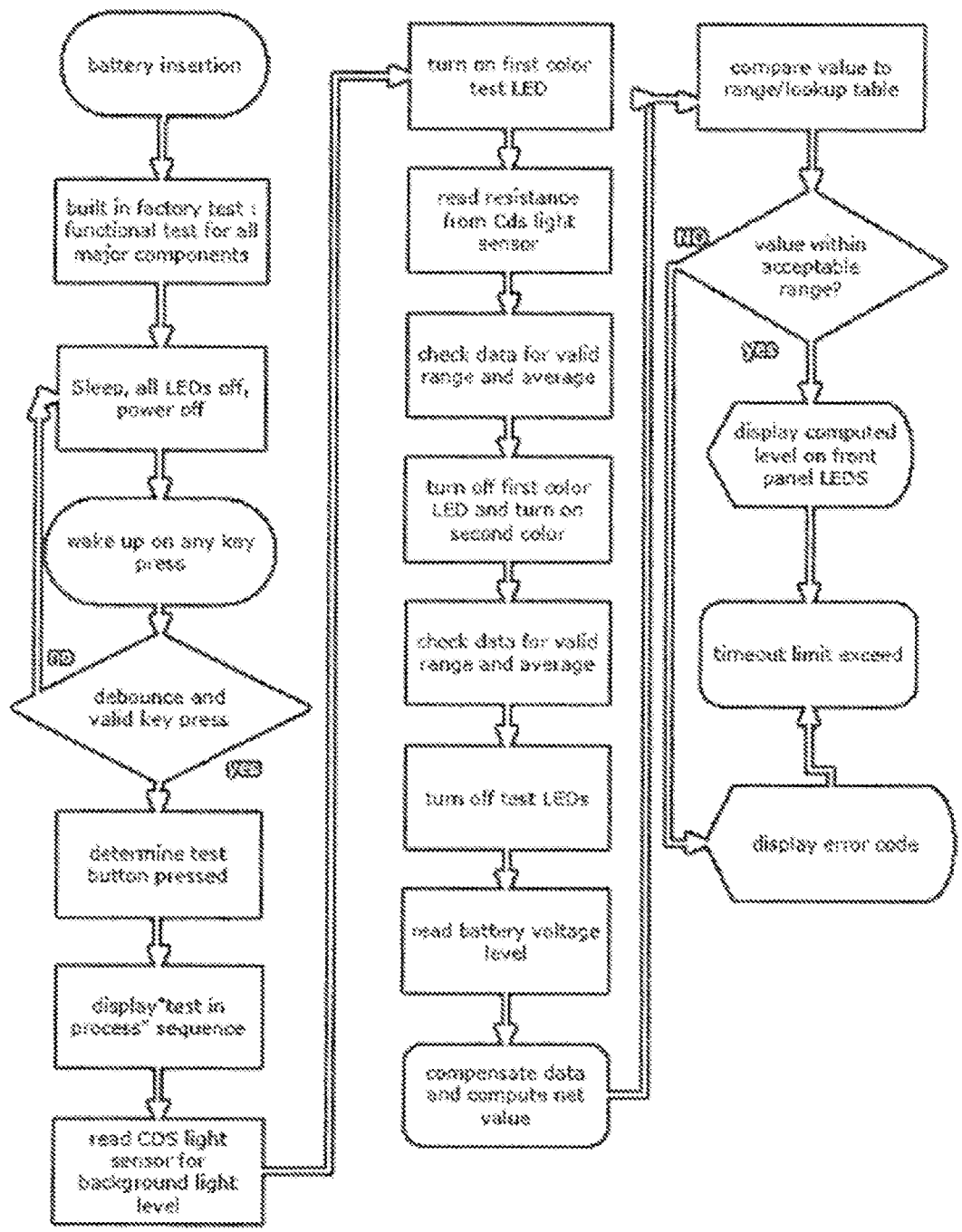
FIG. 6 is a flow diagram illustrating a decision process of the soil tester of the soil testing system of FIG. 1A.

In an exemplary embodiment, and with reference to FIG. 6, various specific tests of soil samples can be conducted by illuminating a first color light source (one of 122a and 122b) reading the light level based upon the resistance of photodetector 124, and deactivating the first color light source and/or illuminating a second color light source (the other of light sources 122a and 122b), reading the light level based upon the resistance of photodetector 124, and thereafter deactivating the second color light source 122a, 122b, 122c.

In this manner, microcontroller 126 can take the two readings and can compute the result based on formulae and/or comparison lookup tables, for example, programmed in memory associated with microcontroller 126. In this way, soil tester 100 can determine the chemical and/or pH makeup of the soil sample. Such results may correspond to known values derived from experimental data, and may be provided in one or more reference tables.

Turning now to FIGS. 7A, 7B, and 7C, a reference list of suggested pH values for soil to support various types of vegetation is provided. For example, azalea flowers are suggested to be supported in soil having a pH between 4.5 and 6.0. Accordingly, a pH value of a soil sample indicated through illumination of a corresponding indicator 116a, 116b, 116c, 116d, 116e, 116f, 116g, may be referenced to determine which types of vegetation may be optimally supported in the sampled soil.

Turning additionally to FIG. 8, a reference list of recommended values for nitrogen, phosphorous, and potassium in soil to support various types of vegetation is provided. For example, a typical lawn is suggested to be supported by soil being devoid of phosphorous and potassium, and having a nitrogen value of 3.75-4.0 oz./ft$^2$. However, such values may be too numerous to associate individually with a corresponding indicator on display interface 115. Accordingly, such values may correspond to one of the relative indicators 116h, 116i, 116j, 116k, 116l to indicate that a soil sample comprises a surplus amount, sufficient amount, adequate amount, deficient amount, or depleted amount of a corresponding nutrient.

Turning to FIG. 8, a reference list of various chemical nutrients commonly found in soil are presented to illustrate the optimal pH range associated with the prevalence of the respective chemicals. In this manner, a user of soil testing system 1000 is provided with a reference through which he or she may take actions with regard to soil from which a sample is tested, for example, adjustment of an acidity level (pH) of soil, or addition and/or reduction of other chemicals present in soil. Accordingly, and referring to FIGS. 9, 10, and 11, reference lists are provided to illustrate the amount of various fertilizing compounds that can be used to adjust soil for pH, nitrates, phosphoric acid, and potash based upon values provided by soil tester 100.

In exemplary embodiments, a substantially large number of measured data points can be taken using controlled known samples and then varying several different factors such as, but not limited to, full tolerance range of key components, positioning within the interior sampling chamber 112, exterior light conditions, and voltage of the power source 129, to name a few. In this manner a set of formulae and/or reference tables can be established for each of the tests that can provide reasonable and/or meaningful results for the user. By way of example, tests for fertilizer chemical can have five different levels from "minimal" to "way too much" and each level can have its own table and/or range limits (as in FIGS. 7A, 7B, and 7C above). The computed values derived from the photosensor resistance value when different colored lights are shown through the user prepared samples can be compared to limit range tables (e.g., five limit table ranges). In exemplary embodiments, the change of color of a sample solution may not behave in a linear manner through the usable range and/or empirically measured data with control samples can be used to derive such tables. In exemplary embodiments, the pH table can have seven levels of interest and/or can be derived similar to the method disclosed herein.

In exemplary embodiments, the various reference tables can take into consideration not only the relative difference between the test light colors, but also the absolute value after compensating for exterior light and/or battery voltage variances.

In exemplary embodiments, to improve reliability of the measurements multiple reads of each color can be taken, analyzed to exclude outlier samples, and then averaged. Further, limits can be set for data acquired that may be beyond the expected range of data. This may be done to address situations where user error occurs such as, but not limited to, errors in the preparation of the sample, pressing the wrong test initiation button for a given sample, incorrectly placed sample tube, using too much and/or too little soil and/or liquid in the sample container and/or failure to follow the prescribed waiting times required for reagents to react thoroughly with soil and/or liquid, to name a few. In exemplary embodiments, a special error code, for example, consisting of flashing lights can be displayed when various error conditions occur.

It will be understood that optical properties of various sample containers, liquids, and/or reagents may present unknown quantities that can affect a beam of light passing therethrough. Accordingly, in embodiments, soil tester 100 may be configured to perform a calibration step by transmitting a beam of light through a sample container, liquid, and/or reagent without a soil sample being present so that only the soil sample represents an unknown quantity during testing. Similarly, soil tester 100 may perform a calibration of the interior sampling chamber 112 devoid of any sample container or other components, for example, to account for optical properties of ambient air in the interior sampling chamber 112.

In exemplary embodiments, the amount of light from a light source can be tied to the current provided to that light source, which in turn can be dependent on the voltage level supplied to that light source. Accordingly, as electric potential of the power source 129 is depleted, the amount of light provided by the light source can be reduced. In exemplary embodiments, soil tester 100 can determine the battery levels and adjust calculations to factor variations in the light source based on voltage levels of the power source 129.

In exemplary embodiments, soil tester 100 can be designed to use the more stable portions of the operational range of photodetector 124 to minimize the effect of resistance tolerance ranges for a given light level. Adjustments to mathematical calculations and reference tables can be made by reading the resistance of the photodetector 124 when installing a sample container and/or modifying the calculations accordingly. This can be done at the factory and/or prior to use and stored in memory and/or this can be done anytime in response to installation of power source 129, and/or this can be done in response to an action by the user.

In exemplary embodiments, the microprocessor can self calibrate with each use by reading the voltage of the power source 129 and/or making the corresponding correction in the computation. The voltage adjustment for each of single color light sources 122a, 122b, 122 can be affected differently by varying the supply voltage so unique adjustments for each color may be required.

In exemplary embodiments, after mixing reagents in a sample container, there can be a prescribed amount of time needed before the test may be valid and/or there can be a maximum amount of time, after which the soil/reagent/liquid solution may no longer give the proper result. Accordingly, soil tester 100 may include a timer that may be built into the soil tester to ensure that after mixing the reagents in the sample container that the appropriate amount of time has passed to conduct the test.

In exemplary embodiments, calibration of soil tester 100 can also include factoring in the baseline light level when no light source 122 is active, the voltage level of the power source 129 and its effect on the amount of light from the light source 122, and/or the general shift in the resistance of the photodetector 124 caused by relatively high variances in the resistance.

In embodiments, sample container 114a and/or interior sampling chamber 112 may incorporate structure configured to inhibit the presence of ambient light during analysis of a sample container in the manner described above, for example, by including an oversized lid configured to inhibit the passage of light thereby into interior sampling chamber 112, or a lid or cap atop interior sampling chamber 112. Additionally or alternatively, sample container 114a and/or interior sampling chamber 112 may incorporate structure configured to control and/or alter a beam of light approaching photodetector 124, for example, one or more reflectors, collectors, and/or beam collimators, to name a few.

It will be understood that any of the steps described can be rearranged, separated, and/or combined without deviated from the scope of the disclosure. For ease, steps are, at times, presented sequentially. This is merely for ease and is in no way meant to be a limitation.

Further, it will be understood that any of the elements and/or exemplary embodiments of the disclosure described can be rearranged, separated, and/or combined without deviated from the scope of the disclosure. For ease, various elements are described, at times, separately. This is merely for ease and is in no way meant to be a limitation.

While the various steps, elements, and/or exemplary embodiments of the disclosure have been outlined above, it is evident that many alternatives, modifications and variations will be apparent to those skilled in the art. The various steps, elements, and/or exemplary embodiments of the disclosure, as set forth above, are intended to be illustrative, not limiting. Various changes may be made without departing from the spirit and scope of the disclosure. Accordingly, the spirit and scope of the present disclosure is to be construed broadly and limited only by the appended claims and not by the foregoing specification.

The invention claimed is:

1. A soil tester, comprising:
 a housing including an interior sampling chamber configured to receive a sample container; and
 a sampling apparatus comprising:
  a photodetector mounted along a portion of the interior sampling chamber and having a variable resistance determined by an intensity of incident light; and
  a light source mounted to the interior sampling chamber in a transmissive orientation relative to the photodetector so that a beam of light can be transmitted from the light source to the photodetector through the interior sampling chamber, wherein the interior sampling chamber is constructed and arranged to retain a solution that changes an intensity of the beam of light transmitted therethrough;

electrical circuitry coupled with the photodetector and configured to measure a change in electrical resistance of the photodetector based upon an intensity of the beam of light transmitted from the light source and through the interior sampling chamber into the photodetector; and a display on the housing responsive to the photodetector.

2. The soil tester of claim 1, wherein the variable resistance of the photodetector is associated with a chemical property of a solution retained in the sample container.

3. The soil tester of claim 2, wherein the chemical property is a pH level of a portion of the solution.

4. The soil tester of claim 2, wherein the chemical property is an amount of nitrate of a portion of the solution.

5. The soil tester of claim 2, wherein the chemical property is an amount of phosphoric acid of a portion of the solution.

6. The soil tester of claim 2, wherein the chemical property is an amount of potash of a portion of the solution.

7. A soil testing system, comprising:
  a soil tester, comprising:
    a housing including an interior sampling chamber;
    a sampling apparatus comprising:
      a photodetector mounted along a portion of the interior sampling chamber and having a variable resistance determined by an intensity of incident light; and
      a light source mounted to the interior sampling chamber in a transmissive orientation to the photodetector so that a beam of light can be transmitted from the light source to the photodetector through the interior sampling chamber;
      electrical circuitry coupled with the photodetector and configured to measure a change in electrical resistance of the photodetector upon receiving the beam of light transmitted from the light source and through the interior sampling chamber, wherein the sampling apparatus is configured such that the beam of light is generated solely by the light source; and
  a sample container receivable in the interior sampling chamber and comprising:
    a soil sample; and
    at least one substance of a group comprising: a liquid, a reagent, and a liquid reagent so that the soil sample dissolves to form a solution in the sample container,
  wherein a light transmissivity of the solution changes as a function of a chemical property of the solution;
  a display on the housing responsive to the photodetector.

8. The system of claim 7, wherein the solution has a light transmissivity determined at least partially by the soil sample.

9. The system of claim 7, wherein the solution has a light transmissivity determined at least partially by the at least one substance of a group comprising: a liquid, a reagent, and a liquid reagent.

10. The system of claim 7, wherein the chemical property is a pH level of the solution.

11. The system of claim 7, wherein the chemical property is an amount of nitrate of the solution.

12. The system of claim 7, wherein the chemical property is an amount of phosphoric acid of the solution.

13. The system of claim 7, wherein the chemical property is an amount of potash of the solution.

14. A method of testing a soil sample, comprising:
  providing a soil tester that comprises a housing including an interior sampling chamber, the soil tester also comprising a sampling apparatus that includes a photodetector mounted along a portion of the interior sampling chamber and a light source mounted to the interior sampling chamber in receptive orientation to the photodetector, the photodetector having a variable resistance determined by a property of incident light generated solely by the light source;
  providing a sample container;
  providing a liquid;
  providing a reagent ;
  providing a soil sample;
  dissolving the soil sample into a solution with the liquid and the reagent in the sample container, wherein the reagent is selected to change a light transmissivity of the solution as a function of a chemical property of the solution;
  inserting the sample container into the interior sampling chamber of the soil tester; and
  activating the at least one light source;
  passing at least a portion of a beam of light through the solution and measuring a property of the portion of the beam of light passing through the solution;
  comparing the parameters of the light to values in a lookup table; and
  displaying test results on a display.

15. The method of claim 14, wherein the chemical property is a pH level of the solution.

16. The method of claim 14, wherein the chemical property is an amount of nitrate of the solution.

17. The method of claim 14, wherein the chemical property is an amount of phosphoric acid of the solution.

18. The method of claim 14, wherein the chemical property is an amount of potash of the solution.

* * * * *